(12) United States Patent
Griffith

(10) Patent No.: US 9,962,085 B2
(45) Date of Patent: May 8, 2018

(54) WIRELESS POWER TRANSFER AND COMMUNICATIONS

(71) Applicant: Alfred E. Mann Foundation for Scientific Research, Santa Clarita, CA (US)

(72) Inventor: Glen A. Griffith, Newbury Park, CA (US)

(73) Assignee: The Alfred E. Mann Foundation For Scientific Research, Santa Clarita, CA (US)

( * ) Notice: Subject to any disclaimer, the term of this patent is extended or adjusted under 35 U.S.C. 154(b) by 464 days.

(21) Appl. No.: 14/814,447

(22) Filed: Jul. 30, 2015

(65) Prior Publication Data

US 2016/0036244 A1 Feb. 4, 2016

Related U.S. Application Data

(60) Provisional application No. 62/031,077, filed on Jul. 30, 2014.

(51) Int. Cl.
*H01F 37/00* (2006.01)
*A61F 2/54* (2006.01)
(Continued)

(52) U.S. Cl.
CPC .............. *A61B 5/0031* (2013.01); *A61F 2/54* (2013.01); *A61F 2/72* (2013.01); *H02J 7/025* (2013.01); *H02J 50/12* (2016.02); *H02J 50/40* (2016.02); *H02J 50/70* (2016.02); *H04B 5/0031* (2013.01); *H04B 5/0037* (2013.01);
(Continued)

(58) Field of Classification Search
CPC ........... A61B 5/0031; A61B 2560/0219; H02J 50/12; H02J 50/40; H02J 50/70; H02J 5/005; H02J 7/025; H02J 17/00; A61F 2/54; A61F 2/72; A61F 2002/701; A61F 2002/704; A61F 2002/705; A61F 2002/7615; H04B 5/0031; H04B 5/0037;
(Continued)

(56) References Cited

U.S. PATENT DOCUMENTS 6,034,651 A 3/2000 Enguent
6,329,808 B1 12/2001 Enguent
(Continued)

FOREIGN PATENT DOCUMENTS

EP 1 738 716 A2 1/2007
WO 02/094370 A1 11/2002

OTHER PUBLICATIONS

International Search Report, International Application No. PCT/US2015/43025, dated Oct. 30, 2015.
(Continued)

*Primary Examiner* — Hal Kaplan
(74) *Attorney, Agent, or Firm* — Alfred Mann Foundation

(57) ABSTRACT

An inductive wireless power transfer and communication system includes an electrostatic shield for one of the coils. The electrostatic shield is inductively coupled with the coil and is configured as an open circuit. A signal processing element or elements, especially a modulator or a demodulator, are connected across the electrical discontinuity in the electrostatic shield. Because the electrostatic shield is inductively coupled to the coil, the modulator or demodulator can operate on the signal on the coil.

48 Claims, 14 Drawing Sheets

(51) Int. Cl.
*A61F 2/72* (2006.01)
*A61B 5/00* (2006.01)
*H02J 7/02* (2016.01)
*H04B 5/00* (2006.01)
*H02J 50/40* (2016.01)
*H02J 50/12* (2016.01)
*H02J 50/70* (2016.01)
*A61N 1/372* (2006.01)
*A61N 1/378* (2006.01)
*A61F 2/70* (2006.01)
*A61F 2/76* (2006.01)

(52) U.S. Cl.
CPC ......... H04B 5/0075 (2013.01); H04B 5/0093 (2013.01); *A61B 2560/0219* (2013.01); *A61F 2002/701* (2013.01); *A61F 2002/704* (2013.01); *A61F 2002/705* (2013.01); *A61F 2002/7615* (2013.01); *A61N 1/3787* (2013.01); *A61N 1/37229* (2013.01)

(58) Field of Classification Search
CPC ................ H04B 5/0075; H04B 5/0093; A61N 1/37229; A61N 1/3787
USPC .......................................... 307/104; 320/108
See application file for complete search history.

(56) References Cited

U.S. PATENT DOCUMENTS

| | | |
|---|---|---|
| 6,542,777 B1 | 4/2003 | Griffith et al. |
| 7,232,767 B2 * | 6/2007 | George ................ H01J 37/321 |
| | | 257/E21.17 |
| 7,260,435 B2 | 8/2007 | Ibrahim |
| 8,413,604 B2 * | 4/2013 | George ................ H01J 37/321 |
| | | 118/723 I |
| 8,660,487 B2 | 2/2014 | Kargl et al. |
| 2003/0201862 A1 | 10/2003 | Arntz et al. |
| 2008/0082143 A1 | 4/2008 | Dai et al. |
| 2011/0086256 A1 * | 4/2011 | Julstrom ................ H01F 38/14 |
| | | 429/121 |
| 2012/0228956 A1 | 9/2012 | Kamata |
| 2014/0111021 A1 | 4/2014 | Nakamura |

OTHER PUBLICATIONS

Written Opinion of the ISA, International Application No. PCT/US2015/43025, dated Nov. 2, 2015.
Active Load Modulation, RFID Handbook, http://rfid-handbook.de/about-rfid/active-load-modulation.html?showall=1&limitstart=, Accessed Jul. 9, 2015.

* cited by examiner

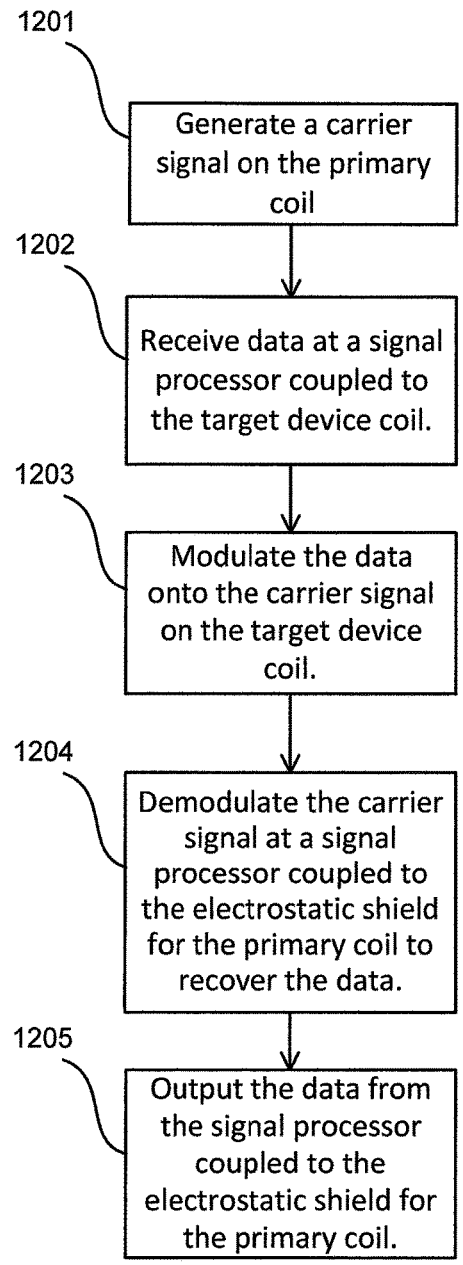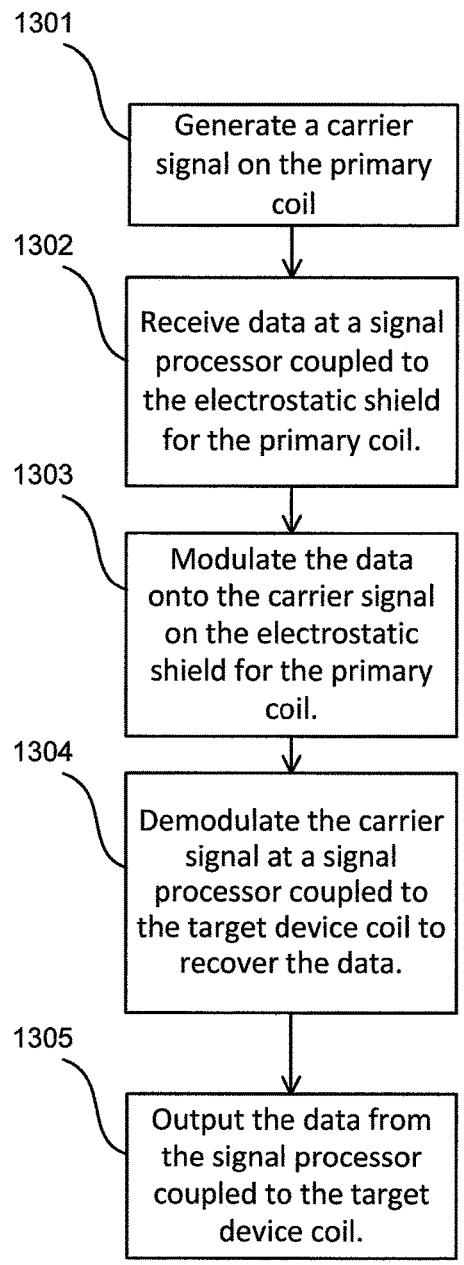
FIG 12
FIG 13

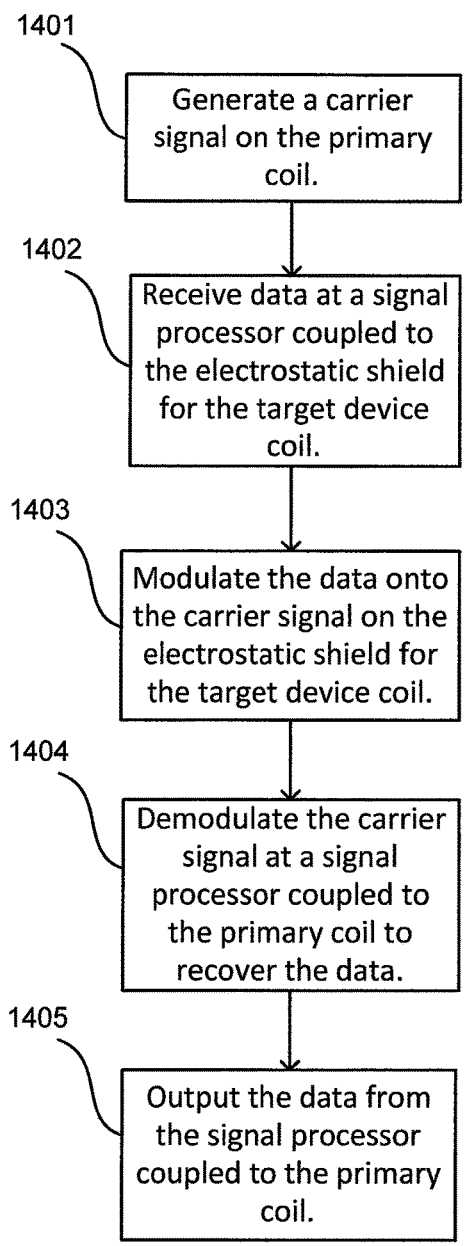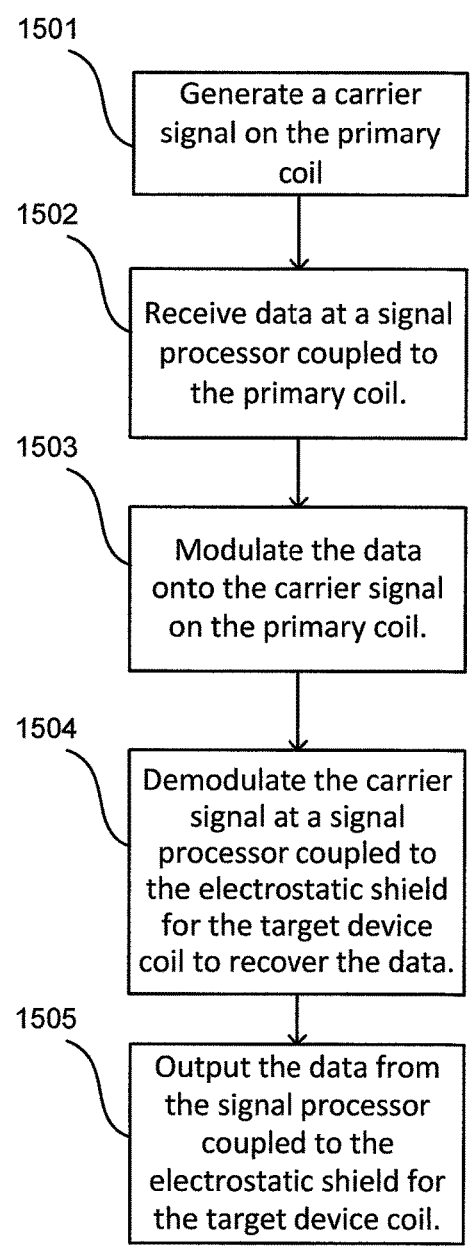
FIG 14
FIG 15

WIRELESS POWER TRANSFER AND COMMUNICATIONS

CROSS REFERENCE TO RELATED APPLICATIONS

The present application claims the benefit under 35 U.S.C. § 119(e) to U.S. Provisional Application No. 62/031, 077, filed on Jul. 30, 2014, which is incorporated herein by reference in its entirety.

BACKGROUND

In the field of wireless power transfer, inductive coupling has been used to provide power to and communicate with a device without making electrical contact. This technique has been used, for example, with implanted medical devices. Systems utilizing this technique have an external unit that is a power transmitter and a medical device implanted within the body of a patient that is a power receiving unit. A coil driver applies an AC signal to a primary coil in the external unit, generating a magnetic field. The power transmitter is placed in proximity to the body of the patient so that the magnetic field induces a current on a secondary coil in the implanted medical device. A power management unit in the implant can use the current induced on the secondary coil to charge a battery or to directly operate the implanted medical device. To provide communication between the coils, the power signal on the secondary coil is load modulated by a modulator. This modulation is picked up by a demodulator attached to the primary coil. Using this method, systems communicate and transmit power on a single inductive link simultaneously.

In these inductive power transfer and communication systems, the coils are susceptible to parasitic capacitances and parasitic conductances. In particular, parasitic variations can be introduced by the presence of tissue near the coils, a circumstance which is presented frequently with implanted medical devices when the external unit is handled or when it is placed near the target implant. These parasitic variations can alter the inductive link between the coils, reducing the efficiency of power transfer or interfering with the communication of data. To address the changes in operation of the inductive link caused by parasitic variations, prior art systems have used frequency shifting or active re-tuning. See Troyk, U.S. Pat. No. 5,179,511; Stover, U.S. Pat. No. 7,190,153. These solutions may address the parasitic variations, but prevent the operation of the system at very fixed frequencies. For regulatory reasons, the use of some compliant technologies (such as near field communication, regulated under ISO/IEC 18092) requires operation at very fixed frequencies.

The coils in inductive power transfer and communication systems usually operate with large currents and/or voltages. Accordingly the modulation elements and demodulation elements applied to these coils need to be able to handle large currents, large voltages, or both. This generally increases the size of the components used to modulate the power signal and increases the stress levels on the components, and requires the demodulator to tolerate a large input signal. This can add to the weight and cost of the device, and reduce the longevity of the device.

Accordingly, there is an ongoing need for inductive power transfer and communication systems that are resistant or immune to parasitic variations introduced externally and that accomplish modulation and demodulation with lesser demands on the modulation and demodulation components.

BRIEF DESCRIPTION OF THE DRAWINGS

FIG. 12 is a flow chart depicting an exemplary embodiment of a method of communicating between two coils according to the invention.

FIG. 13 is a flow chart depicting an exemplary embodiment of a method of communicating between two coils according to the invention.

FIG. 14 is a flowchart depicting an exemplary embodiment of a method of communicating between two coils according to the invention.

FIG. 15 is a flowchart depicting an exemplary embodiment of a method of communicating between two coils according to the invention.

SUMMARY

An inductive wireless power transfer and communication system includes an electrostatic shield for one of the coils. The electrostatic shield is inductively coupled with the coil and is configured as an open circuit. A signal processing element or elements, especially a modulator or a demodulator, are connected across the electrical discontinuity in the electrostatic shield. Because the electrostatic shield is inductively coupled to the coil, the modulator or demodulator can operate on the signal on the coil.

DETAILED DESCRIPTION

In this Detailed Description, the claims below, and in the accompanying drawings, reference is made to particular features (including method steps) of embodiments of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular embodiments of the invention, and in the invention generally.

Figure 1A:
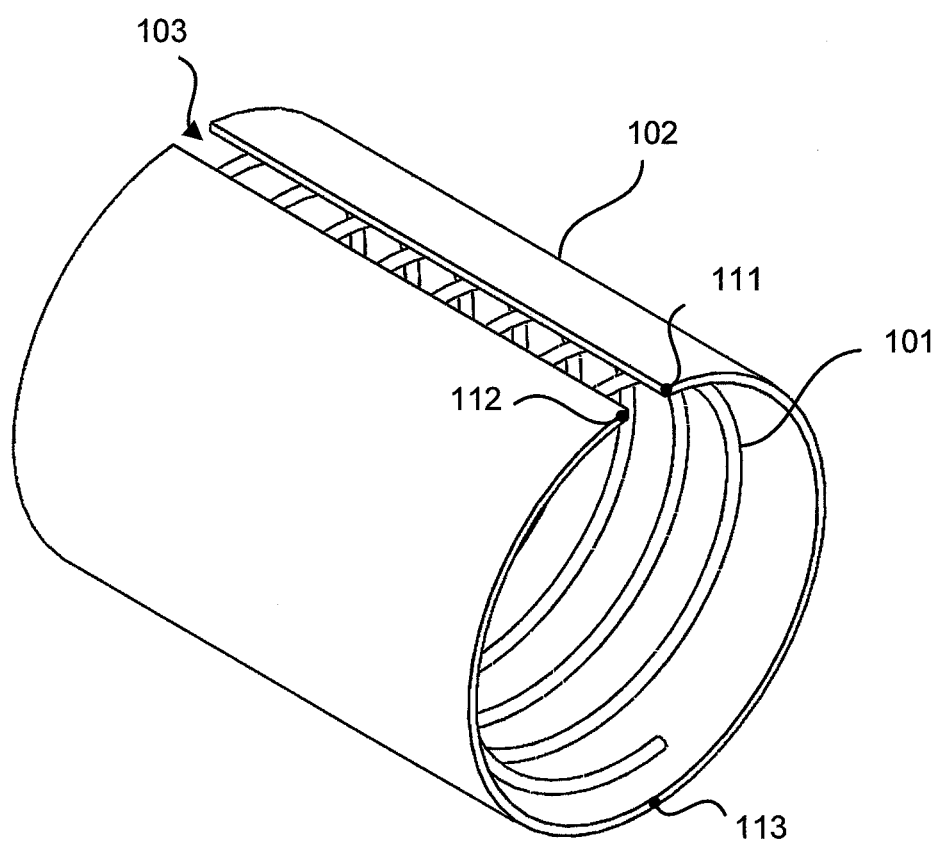
FIG. 1A depicts an exemplary embodiment of a coil and shield according to the invention.

FIG. 1A shows an exemplary embodiment of a coil and a shield according to the present invention. A primary coil 101 is surrounded by a coil guard 102. The primary coil 101 and the coil guard 102 are not in electrical contact. An insulator may be placed between the primary coil 101 and the coil guard 102, and the coil guard 102 and/or the primary coil 101 could be electrically insulated. The coil guard 102 is an electrostatic shield for the primary coil 101 which protects the primary coil 101 from external parasitic effects. Because the electrostatic shield 102 is structured as a close-fitting conductive sheath that is axially aligned with the primary coil 101, it inductively couples with the primary coil 101 when the primary coil 101 generates a magnetic field. The primary coil 101 and the electrostatic shield 102 effectively operate similar to a transformer, with the electrostatic shield 102 being a single turn secondary coil. If the electrostatic shield 102 completely encircled the coil 101, it would act as a shorted turn, dissipating energy and altering the operation of the inductive link between the primary coil 101 and the target coil. To avoid this, the electrostatic shield 102 has a gap 103 extending the axial length of the electrostatic shield 102 which prevents current from circulating. The electrostatic shield 102 is configured as an open circuit, wherein the gap 103 is the conductive discontinuity. The gap 103 does not need to be a gap in the protection of the electrostatic shield 102, it need only be a conductive discontinuity preventing induced current from circulating in the electrostatic shield 102. Although the electrostatic shield 102 shields the primary coil 101 from parasitic variations, the coupling between the electrostatic shield 102 and the primary coil 101 causes changes in the impedance of the electrostatic shield 102 to show up as an effective change in the impedance of the primary coil 101.

To connect electrical components across the primary coil 101, connection is made at the opposite ends of the coil. To connect electrical components across the electrostatic shield 102, connection is made at the opposite sides 111 and 112 of the gap 103. The electrostatic shield may also be center tapped by connecting to a point 113 substantially opposite the gap 103. The electrostatic shield can be configured in a balanced or unbalanced configuration. For a balanced configuration, the electrostatic shield can be grounded at the center tap point 113. Connecting at different points along the axial length of the electrostatic shield 102 can yield different electrical characteristics for the electrostatic shield 102 which can easily be tested and accounted for. In preferred embodiments, connections to the opposite sides 111 and 112 of the gap 103 and to the center tap 113 are all made along one open end of the electrostatic shield 102 to facilitate making connection to associated electronic systems.

Figure 1B:
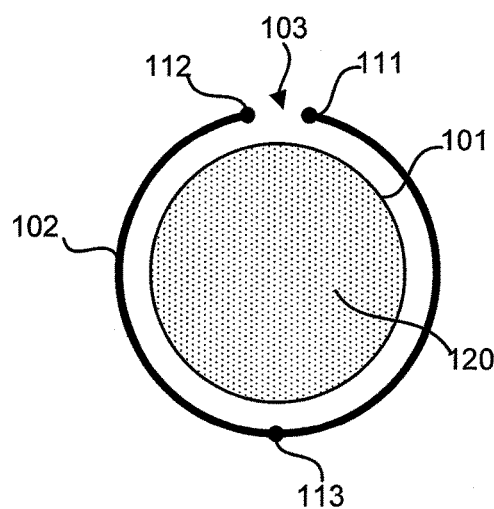
FIGS. 1B-F depict side views of the exemplary embodiment of a coil and shield of FIG. 1A.

FIGS. 1B, 1C, 1D, 1E and 1F depict side views of the coil and shield of FIG. 1A. FIG. 1B shows the location of the primary coil 101, the electrostatic shield 102, the gap 103, the sides of the gap 111 and 112, and the center tap 113. It also depicts the magnetic field 120 generated inside the primary coil 101. These elements are present in FIGS. 1C, 1D, 1E and 1F, though they may not be labeled there.

Figure 1C:
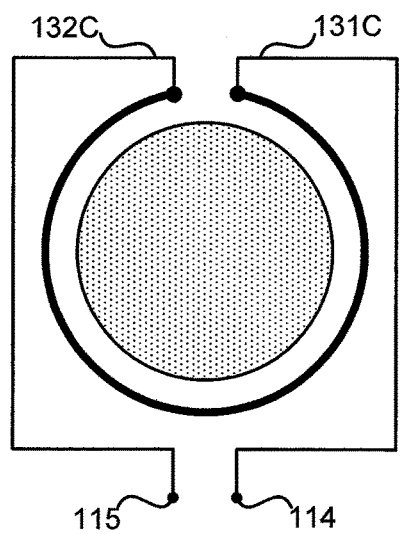

Attention must be paid to the wires connecting the electrostatic shield 102 to associated electronic systems. A first wire 131C, 131D, 131E and 131F in respective FIGS. 1C, 1D, 1E and 1F connects point 111 to an associated electronic system at point 114, and a second wire 132C, 132D, 132E and 132F in respective FIGS. 1C, 1D, 1E and 1F connects point 112 to an associated electronic system at point 115. To inductively couple with the primary coil 101, the electrostatic shield 102 and each pair of wires 131C-132C, 131D-132D, 131E-132E and 131F-132F in respective FIGS. 1C, 1D, 1E and 1F must form a loop which encloses at least part of the magnetic field 120 generated inside the primary coil 101. In embodiments, associated electronic systems coupled to the electrostatic shield 102 are placed substantially opposite the gap 103. If, as shown in FIG. 1C, the wires 131C and 132C are routed away from the gap 103 and around the diameter of the electrostatic shield 102, then none of the magnetic field 120 inside the primary coil 101 will be enclosed so the electrostatic shield 102 and the primary coil 101 will not inductively couple.

Figure 1D:
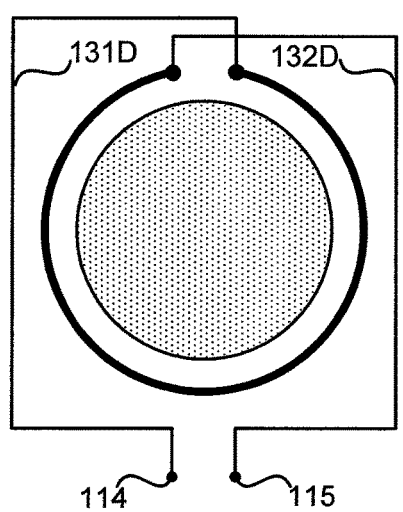

In FIG. 1D, wires 131D and 132D are routed across the gap 103 and around the diameter of the electrostatic shield 102 to reach the associated electronic systems at points 114 and 115. Wire 131D, wire 132D, and the electrostatic shield 102 form a continuous loop between points 114 and 115 that encloses the magnetic field 120. Accordingly, the electrostatic shield 102 and the primary coil 101 are inductively coupled. Because the wire 131D, wire 132D, and the electrostatic shield 102 actually encircle the magnetic field 120 twice, the signal between points 114 and 115 will be double what it would be if the magnetic field 120 was only encircled once.

Figure 1E:
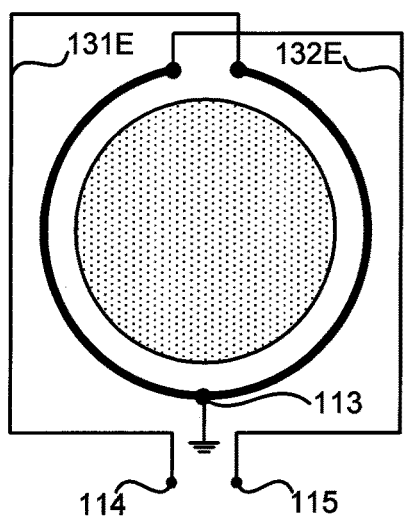

In FIG. 1E, wires 131E and 132E are routed across the gap 103 and around the diameter of the electrostatic shield 102 to reach the associated electronic systems at points 114 and 115. The electrostatic shield 102 is grounded at the center tap 113. The portion of the electrostatic shield 102 between points 113 and 111 and wire 131E substantially enclose the magnetic field 120. Similarly, the portion of the electrostatic shield 102 between points 113 and 112 and wire 132E substantially enclose the magnetic field 120. Accordingly, the electrostatic shield 102 and the primary coil 101 are inductively coupled.

Figure 1F:
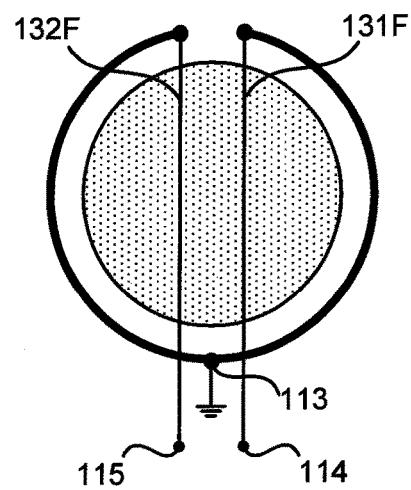

FIG. 1F depicts an embodiment in which wires 131F and 132F are routed directly to points 114 and 115 respectively, without going around the circumference of the electrostatic shield 102. The portion of the electrostatic shield 102 between points 113 and 111 and wire 131F enclose a portion of the magnetic field 120, but not the entire field. The portion of the electrostatic shield 102 between points 113 and 112 and wire 123F enclose a portion of the magnetic field 120, but not the entire field. Because at least a portion of the magnetic field 120 is enclosed, the primary coil 101 and electrostatic shield 102 would still inductively couple. This may be suitable for some embodiments.

Figure 1G:
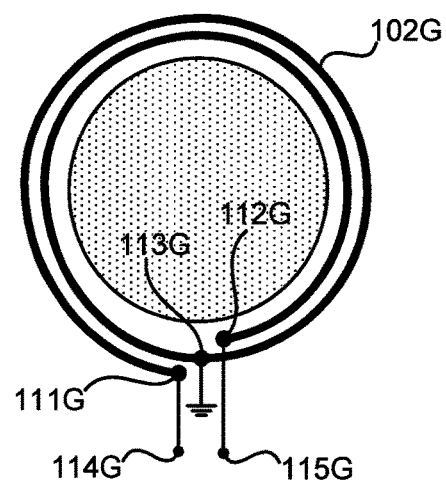
FIG. 1G depicts an exemplary embodiment of a coil and shield according to the invention.

FIG. 1G depicts an alternative embodiment of a coil and a shield according to the invention. Terminal points 114G and 115G connect respective points 111G and 112G to an associated electronic system. In FIG. 1G, the electrostatic shield 102G guarding the primary coil 101 wraps around the primary coil twice, but does not make electrical contact with itself, so the gap 103 is still present between point 111G and point 112G. The electrostatic shield 102G is grounded at the center tap 113G. The portion of the electrostatic shield 102G between points 113G and 111G substantially encloses the magnetic field 120. The portion of the electrostatic shield 102G between the points 113G and 112G substantially encloses the magnetic field 120. Accordingly, the electrostatic shield 102G and the primary coil 101 are inductively coupled.

Figure 2:
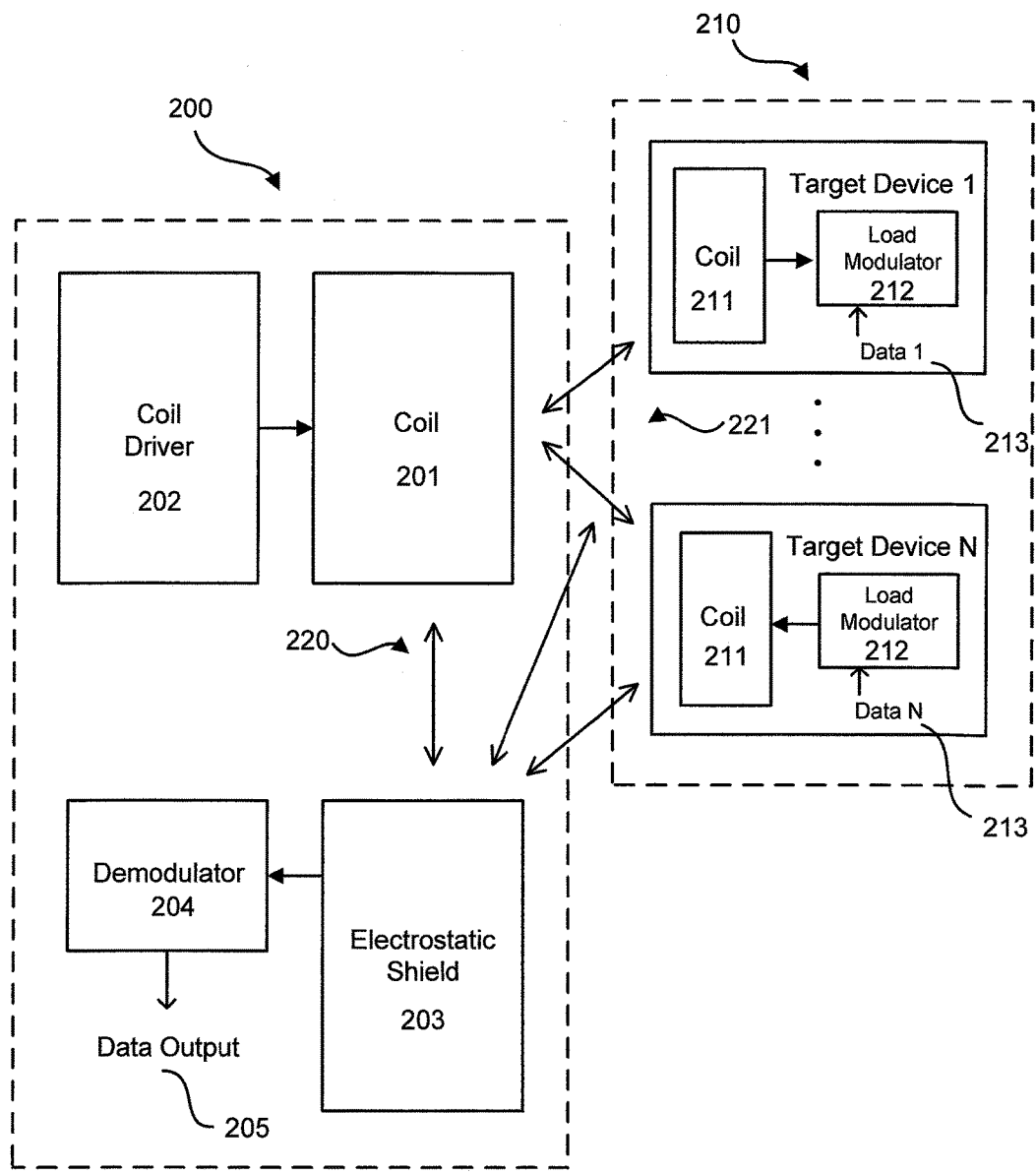
FIG. 2 is a block diagram of an exemplary embodiment of a wireless power transfer and communication system according to the invention.

FIG. 2 shows a block diagram demonstrating how the elements of an exemplary embodiment of a wireless power and communication system interact according to the invention. This embodiment provides power to and uplinks data from one or more target devices 210. The system includes a power transmitting unit 200 and one or more target devices 210. The power transmitting unit 200 includes a primary coil 201 and an electrostatic shield 203. The primary coil 201 is connected to a coil driver 202. The primary coil 201 is inductively coupled to the electrostatic shield 203 through inductive link 220. A demodulator 204 is connected to the electrostatic shield 203 and has a data output 205. The target devices 210 each include a coil 211. The primary coil 201 of the power transmitting unit 200 is inductively coupled to the target device coils 211 through inductive links 221. Preferably, the link 221 between the primary coil 201 of the power transmitting unit 200 and the target device coils 211 is a resonant inductive link. The target device coils 211 are attached to load modulators 212 which have data inputs 213, wherein these data inputs 213 may be configured to receive digital data.

Figure 3:
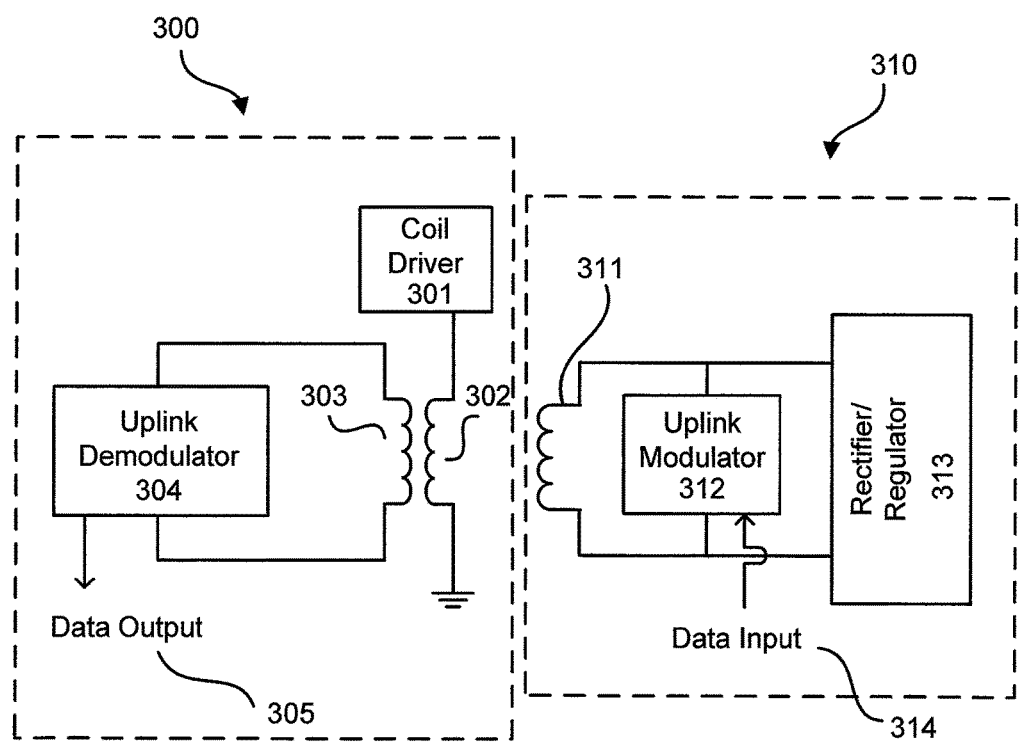
FIG. 3 is a diagram of an exemplary embodiment of a wireless power transfer system with uplink communication according to the invention.

FIG. 3 is a diagram of the exemplary wireless power and communication system of FIG. 2. It depicts the power transmitting unit 300 and one target device 310. The electrostatic shield and connecting wires are represented as an inductor 303. The uplink demodulator 304 is coupled across the gap of the electrostatic shield 303. The electrostatic shield 303, the primary coil 302, and the target device coil 311 are inductively coupled.

The coil driver 301 is coupled to the primary coil 302. The coil driver 301 applies an AC drive signal to the primary coil 302. This results in a carrier signal on the primary coil 302. Because the primary coil 302 is inductively coupled to the target device coil 311 and the electrostatic shield 303, the carrier signal is a function of the characteristics of all three inductors and the loads across them, and is present on all three inductors.

A rectifier and regulator 313 are coupled to the target device 310, and rectify and regulate the carrier signal received on the target device coil 311 to use as power. The uplink modulator 312 is coupled to the target device coil 311 and receives uplink data at the data input 314. To communicate, the uplink modulator 312 alters the carrier signal. The uplink modulator 312 may, for example, amplitude modulate the carrier signal. Preferably, the uplink modulator 312 changes the load presented on the target device coil 311, resulting in a change in the carrier signal. Because the carrier signal is present on all three inductors 302, 303, and 311, changes modulated onto the carrier signal by the uplink modulator 312 on the target device coil 311 appear at the uplink demodulator 304 coupled across the gap of the electrostatic shield 303. The uplink demodulator 304 may therefore demodulate the carrier signal to recover and output the uplink data at the data output 305. When multiple target devices 310 are used, the rectifiers and regulators 313 in each target device 310 may continually rectify and regulate the carrier signal for power, and the system may use time-division multiplexing to communicate between the uplink modulators 312 and the uplink demodulator 304 separately.

Figure 4:
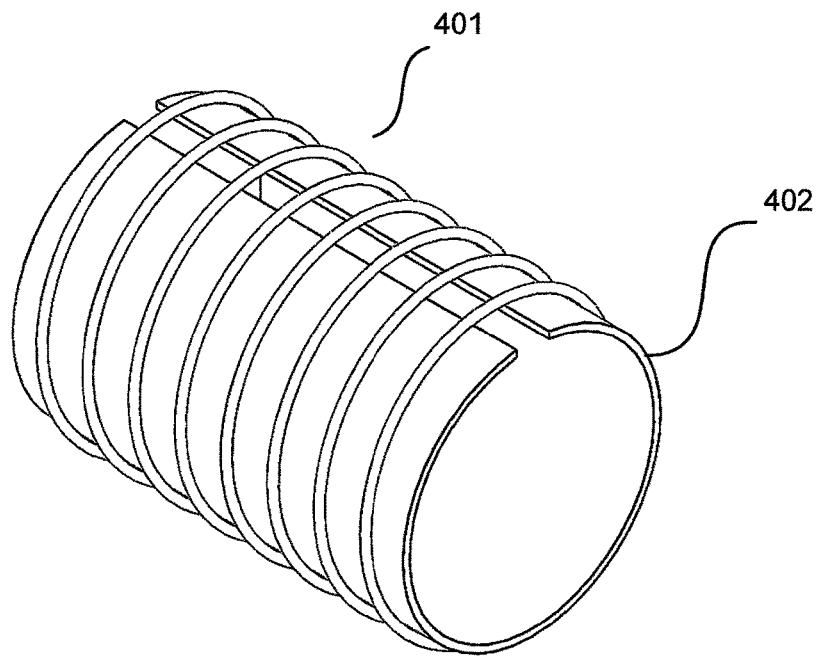
FIG. 4 depicts an exemplary embodiment of a coil and shield according to the invention.
Figure 5:
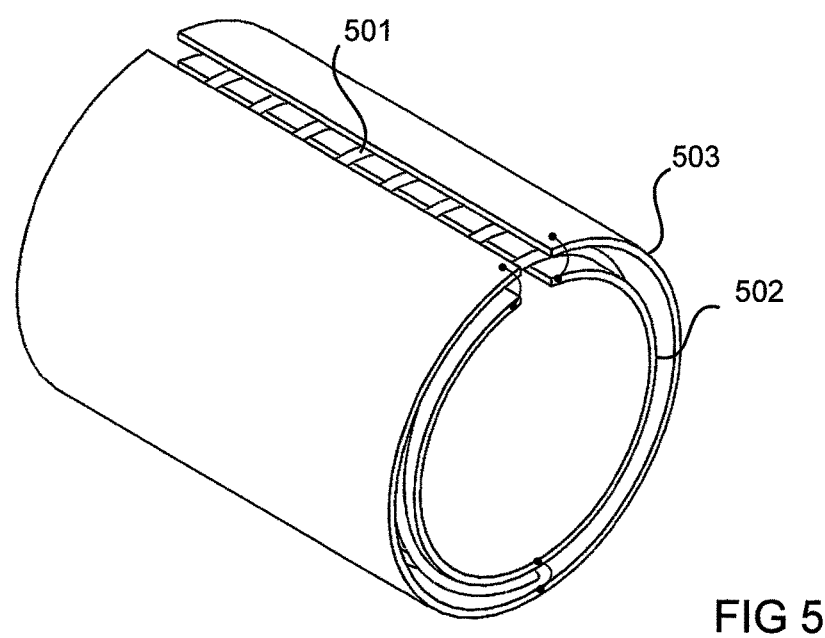
FIG. 5 depicts an exemplary embodiment of a coil and shield according to the invention.

FIGS. 4 and 5 depict alternative embodiments of a coil and shield according to the present invention. In FIG. 4, the electrostatic shield 402 is adjacent to the inner surface of the coil 401, extends circumferentially around the inner surface of the coil 401, and is open on both ends. In this configuration, the electrostatic shield 402 protects the coil 401 from parasitic variations presented by objects inside the coil 401. In FIG. 5, the coil 501 has an electrostatic shield portion 502 conforming to the inner surface of the coil 501 and an electrostatic shield portion 503 conforming to the outer surface of the coil, to protect from parasitic variations originating from either direction. The outer shield 503 is adjacent to the outer surface of the coil 501 and surrounds the coil 501 circumferentially. The inner shield 502 is adjacent to the inner surface of the coil 501 and extends around the inner surface of the coil 501 circumferentially. In embodiments, the two shields 502 and 503 are electrically coupled together such that they act as a single inductive element. This can be accomplished by connecting each side of a gap to the corresponding side of the other gap as shown in FIG. 5. Other parts of the two electrostatic shields 502 and 503 may be connected, such as connecting the center tap terminals.

A coil and shield according to the invention may both be cylindrical as shown. They may also taper from one end to the other, which may result in a truncated conical structure, or may otherwise be irregularly shaped. In a preferred embodiment, the coil and shield conform to the shape of a residual portion of an amputated limb.

Figure 6:
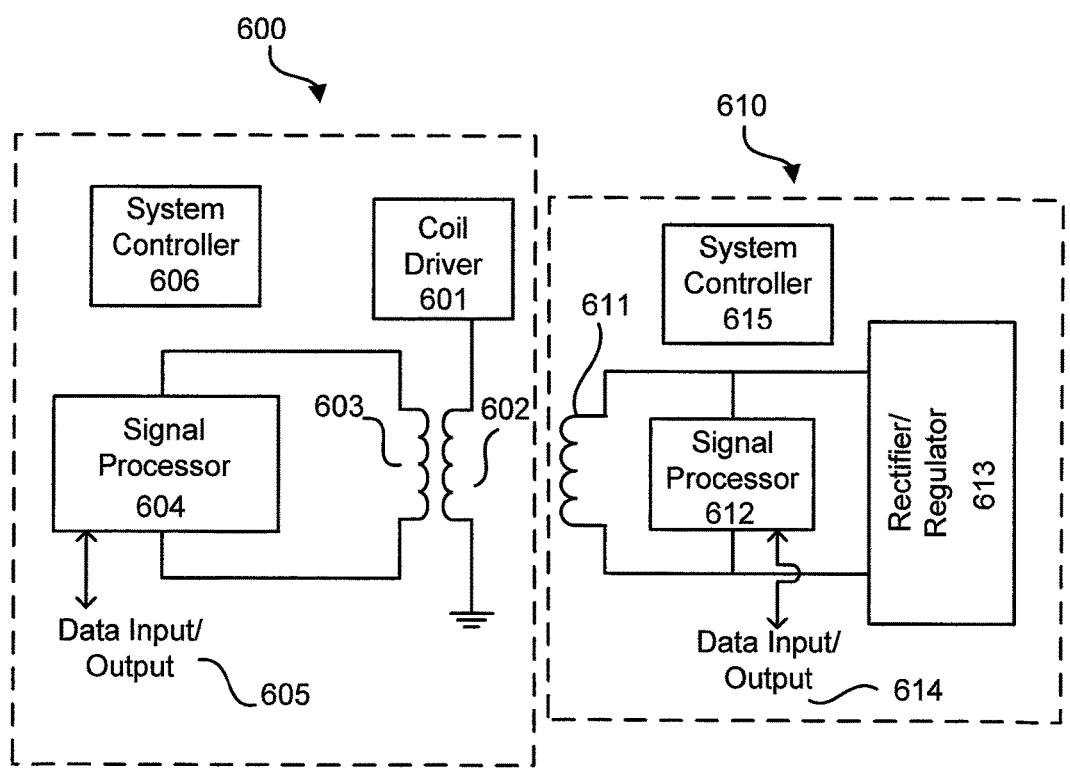
FIG. 6 is a diagram of an exemplary embodiment of a wireless power transfer and communication system according to the invention.

FIG. 6 is a circuit diagram of an alternative embodiment of a wireless power transfer and communication system according to the invention. FIG. 6 includes a power transmitting device 600 and a target device 610. The power transmitting device 600 includes an electrostatic shield 603 guarding a primary coil 602. This embodiment makes use of a power transmitter signal processor 604 and a target signal processor 612. The target signal processor 612 is attached to the target device coil 611, and the power transmitter signal processor 604 is attached across the gap of the electrostatic shield 603. A rectifier and regulator 613 are attached to the target device coil 611 to capture power. The primary coil 602, the target device coil 611, and the electrostatic shield 603 are inductively coupled.

A coil driver 601 is coupled to the primary coil 602, and applies an AC drive signal to the primary coil 602. This results in a carrier signal on the primary coil 602. Because the primary coil 602 is inductively coupled to the target device coil 611 and the electrostatic shield 603, the carrier signal is a function of the characteristics of all three inductors and the loads across them, and is present on all three inductors.

As was discussed regarding the uplink modulator 312 and demodulator 304 in FIG. 3, the power transmitter signal processor 604 and the target signal processor 612 can communicate by modulating and demodulating the carrier signal. To provide uplink communication, uplink data would be applied to the data input/output 614 of the target signal processor 612. The target signal processor 612 would modulate the carrier signal with the uplink data, preferably by modifying the impedance presented across the target device coil 611, thereby changing the carrier signal on all three inductors. The power transmitter signal processor 604 would demodulate the carrier signal on the electrostatic shield 603, outputting the uplink data at its data input/output 605. The modulation may be, for example, amplitude modulation.

To provide downlink communication, the power transmitter signal processor 604 would modulate the carrier signal, preferably by changing the impedance presented across the gap of the electrostatic shield 603. The modulated carrier signal could then be demodulated by the target signal processor 612, and the target signal processor 612 would output the downlink data at its data input/output 614. The modulation may be, for example, amplitude modulation.

It is further contemplated that half-duplex bidirectional communication could be accomplished in the present embodiment by using multiplexing techniques known in the art. The power transmitting device 600 includes a system controller 606, and the target device 610 includes a system controller 615. The system controllers 606 and 615 may be configured to control their respective signal processors 604 and 612. During periods when uplink communication is to be performed, system controller 606 could control signal processor 604 to operate as a demodulator and system controller 615 could control signal processor 612 to operate as a modulator. During periods when downlink communication is to be performed, system controller 606 could control signal processor 604 to operate as a modulator and system controller 615 could control signal processor 612 to operate as a demodulator.

Figure 7:
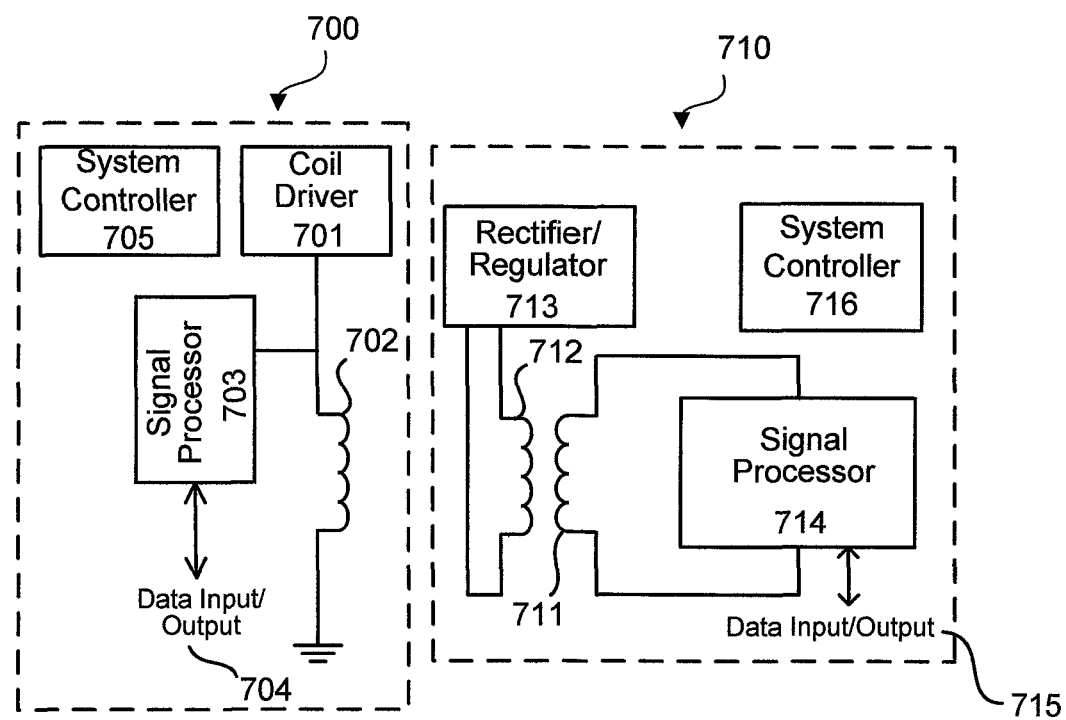
FIG. 7 is a diagram of an exemplary embodiment of a wireless power transfer and communication system according to the invention.

FIG. 7 is a circuit diagram of an alternative embodiment of a wireless power transfer and communication system according to the invention. FIG. 7 includes a power transmitting device 700 and a target device 710. In this embodiment, the electrostatic shield 711 is shielding the target device coil 712. A target signal processor 714 with a data input/output 715 is attached across the gap of the electrostatic shield 711. A rectifier and regulator 713 are attached to the target device coil 712 to capture power. The target device 710 includes a system controller 716. The primary coil 702, the target device coil 712, and the electrostatic shield 711 are inductively coupled.

The power transmitting device 700 includes a system controller 705. The coil driver 701 and a power transmitter signal processor 703 with a data input/output 704 are coupled to the primary coil 702. The coil driver 701 applies an AC drive signal to the primary coil 702. This results in a carrier signal on the primary coil 702. Because the primary coil 702 is inductively coupled to the target device coil 712 and the electrostatic shield 711, the carrier signal is a function of the characteristics of all three inductors and the loads across them, and is present on all three inductors. Accordingly, the power transmitter signal processor 703 and the target signal processor 714 can perform uplink, downlink, or half-duplex bidirectional communication as discussed regarding the system of FIG. 6, but with the electrostatic shield 711 guarding the target coil 712 instead of the primary coil 702. It is also further contemplated that electrostatic shields could be applied to both the primary coil and the target device coil with separate signal processors applied to the gaps of the electrostatic shields.

Figure 8:
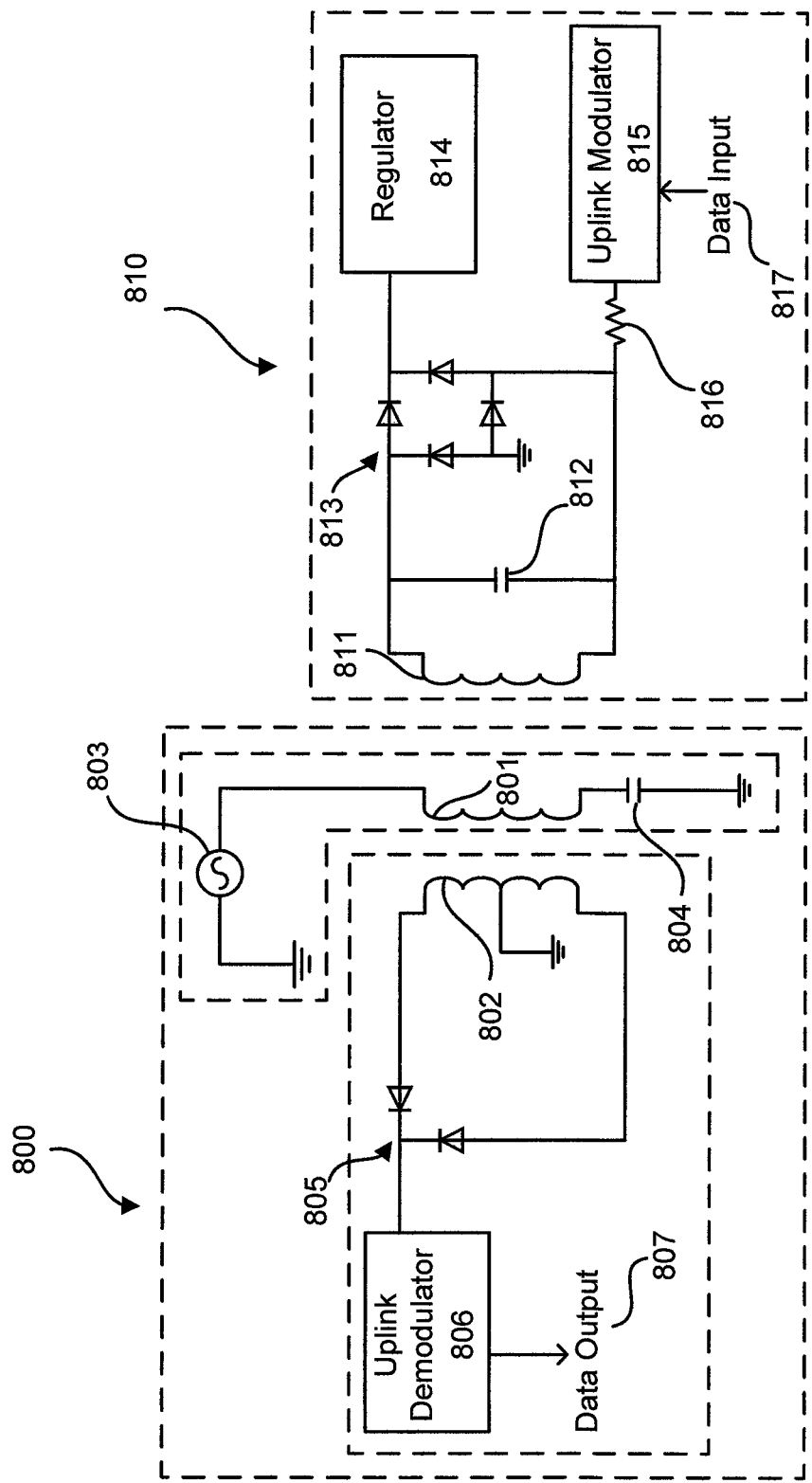
FIG. 8 is a circuit diagram of an embodiment of a wireless power transfer and communication system according to the invention.

FIG. 8 is a circuit diagram of an exemplary embodiment of a transcutaneous power transfer and communication system according to the invention. This embodiment includes an external unit 800 and one or more implanted medical devices 810. The implanted medical devices 810 are preferably implanted into a limb of a patient. The external unit 800 includes a primary coil 801 and an electrostatic shield 802 shielding the primary coil 801.

Figure 9:
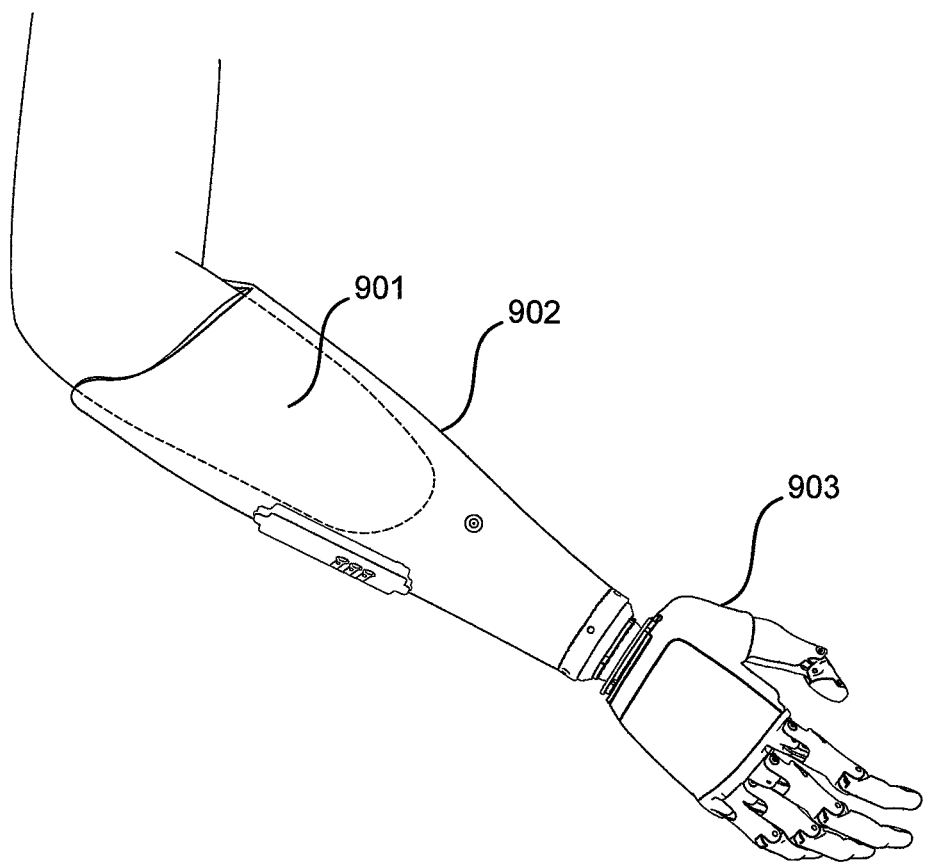
FIG. 9 is a diagram of an exemplary embodiment of a system using a wireless power transfer and communication system according to the invention.

The external unit 800 is preferably sized to fit the primary coil 801 and the electrostatic shield 802 around the limb of the patient. As depicted in FIG. 9, the limb may be a residual portion 901 of an amputated limb, and the external unit 800 may be a controller 902 for a bionic prosthesis 903. The system may be an IMES® type system, in which the implanted medical devices 810 are sensors configured to detect muscle contraction, for example by monitoring electromyogram (EMG) signals, of muscles in a residual limb 901, the controller 902 may be fitted to surround the residual limb 901, delivering power to the sensors and receiving communication from the sensors regarding detected muscle contraction, and the bionic prosthesis 903 may be a robotic hand configured to move in response to the communications received from the sensors, allowing the patient to control the robotic hand by attempting to contract the muscles in the residual limb 901. Different muscles or different portions of muscles would correspond to independently movable parts of the prosthesis 903. When the sensors 810 detected contraction in a muscle or a portion of a muscle, it would communicate to the controller 902 through the wireless power transfer and communication circuitry that the muscle or portion of a muscle was contracted. The controller 902 would then control the prosthesis 903 to move the independently moveable part that corresponded with the muscle that was contracted. In preferred embodiments, the sensor 810 would communicate the magnitude of contraction, and the controller 902 would control the prosthesis 903 to move the independently moveable part according to the magnitude of the contraction.

The electrostatic shield 802 may be inside the coil 801, as in FIG. 4, to protect the coil 801 from parasitic variations introduced by the limb. The electrostatic shield 802 may be outside the coil 801, as in FIG. 1, to protect the coil 801 from parasitic variations introduced by handling the external unit. Preferably, the coil 801 is shielded both inside and outside, as in FIG. 5, to address both cases. The coil 801 and the electrostatic shield 802 may be cylindrical, or may be shaped to generally conform to the limb.

The electrostatic shield 802 is center-tapped by grounding a terminal opposite the gap. A rectifier 805 is attached across the gap of the electrostatic shield 802 with an uplink demodulator 806 coupled to the output of the rectifier 805. A capacitor 804 is attached to the primary coil 801 to form a power transmitter LC tank circuit. Alternatively, the primary coil 801 could have no capacitor but could be driven at or near the self-resonant frequency of the primary coil 801. A coil driver 803 applies an AC drive signal to the primary coil 801, causing a carrier signal on the primary coil 801. In preferred embodiments, the operating frequency is in the 13.56 MHz±7 kHz band standardized for NFC devices according to ISO/IEC 18092. The carrier signal on the primary coil 801 generates the magnetic field which will power and communicate with the implants 810 inside the limb.

The one or more implanted medical devices 810 each have a target device coil 811. A capacitor 812 is attached in parallel with the target device coil 811 to form a receiver LC tank circuit. The power transmitter LC circuit and the receiver LC tank circuit are inductively coupled and tuned to form a resonant inductive link. A rectifier 813 is attached across the receiver LC tank circuit. The output of the rectifier 813 delivers the rectified carrier signal to a regulator 814 to power or charge a battery of the implant 810. An uplink modulator 815 receives an uplink data signal, for example indicative of detected muscle contraction, at the data input 817 and load modulates the carrier signal with the uplink data by coupling a load modulation resistor 816 to the receiver coil 811. The modulated carrier signal is demodulated by the uplink demodulator 806 on the electrostatic shield 802, and the uplink demodulator 806 outputs the uplink data signal at the data output 807. The data output may be coupled to a prosthetic controller 902.

Figure 10:
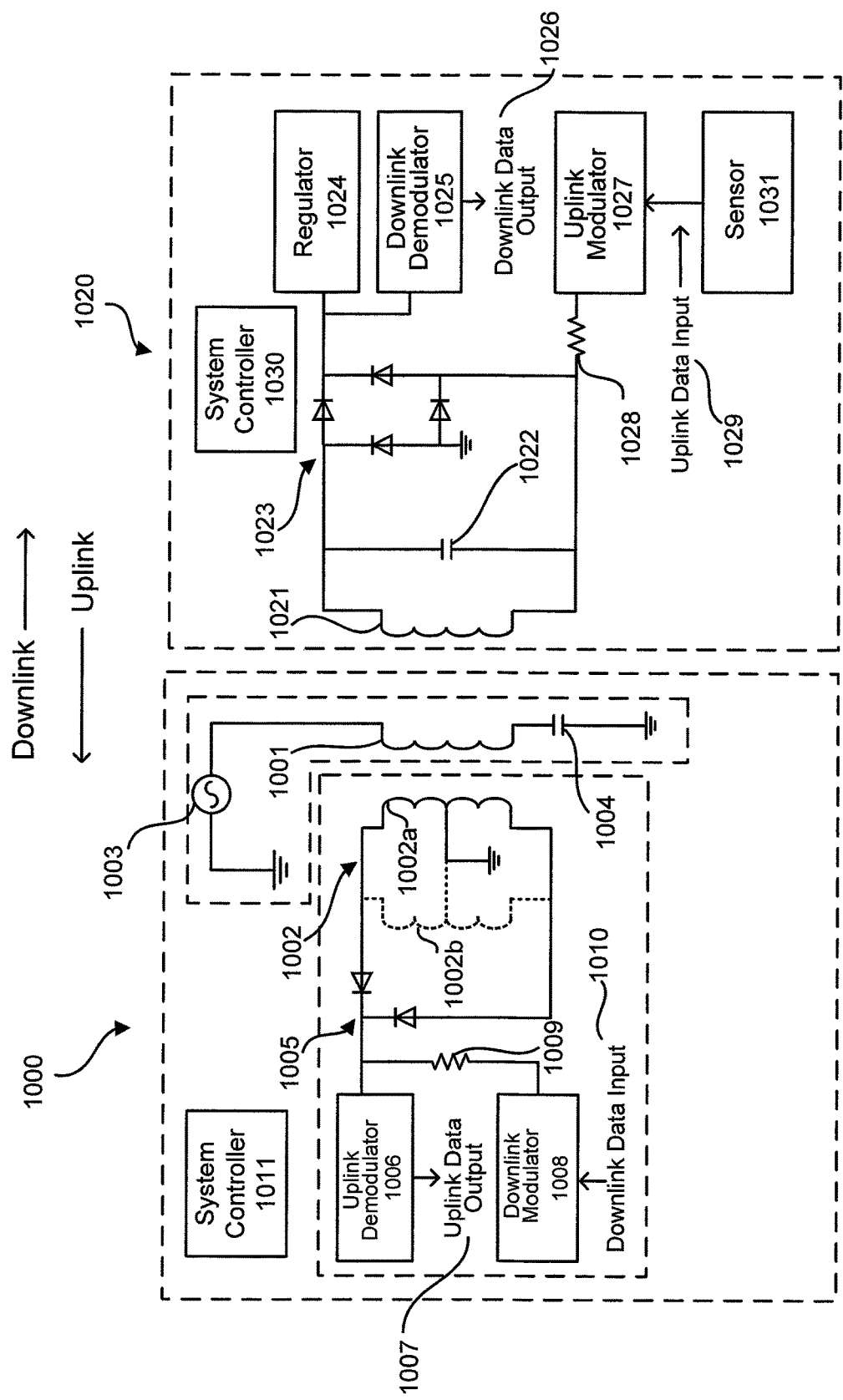
FIG. 10 is a circuit diagram of an embodiment of a wireless power transfer and communication system according to the invention.

FIG. 10 is a circuit diagram of an exemplary embodiment of a transcutaneous power transfer and communication system according to the invention. This embodiment includes an external unit 1000 and one or more target devices 1020. The external unit 1000 includes a primary coil 1001 and an electrostatic shield 1002 guarding the primary coil 1001.

The electrostatic shield 1002 has a portion guarding the inside of the primary coil 1001 and a portion guarding the outside of the primary coil 1001, as depicted in FIG. 5, with the two portions coupled together at each side of the gap and at the center tap. This arrangement may be modeled as a single equivalent inductor 1002a, or as two parallel inductors 1002a and 1002b. The center tap terminal is grounded. A rectifier 1005 is attached across the gap of the electrostatic shield 1002. An uplink demodulator 1006 is coupled to the output of the rectifier 1005. A downlink modulator 1008, with a load modulation resistor 1009, is also coupled to the output of the rectifier 1005.

A capacitor 1004 is attached to the primary coil 1001 to form a power transmitter LC tank circuit. Alternatively, the primary coil could have no capacitor but could be driven at or near the self-resonant frequency of the primary coil 1001. A coil driver 1003 applies an AC drive signal to the primary coil 1001, causing a carrier signal on the primary coil 1001. The carrier signal on the primary coil 1001 generates the magnetic field which will power and communicate with the target devices 1020.

The one or more target devices 1020 each have a target device coil 1021. A capacitor 1022 is attached in parallel with the target device coil 1021 to form a receiver LC tank circuit. The power transmitter LC circuit and the receiver LC tank circuit are inductively coupled and tuned to form a resonant inductive link. A rectifier 1023 is attached across the receiver LC tank circuit. The output of the rectifier 1023 delivers the rectified carrier signal to a regulator 1024 to power or charge a battery of the target device 1020. A downlink demodulator 1025 is coupled to the output of the rectifier 1023. An uplink modulator 1027, with a load modulation resistor 1028, is also coupled to the output of the rectifier 1023.

During uplink periods, the uplink modulator 1027 receives an uplink data signal at the uplink data input 1029 and load modulates the carrier signal with the uplink data by coupling the load modulation resistor 1028 to the target device coil 1021. In preferred embodiments, a sensor 1031 is coupled to the uplink data input 1029, and the uplink data modulator 1027 modulates the carrier signal with sensor data received from the sensor 1031. The sensor 1031 may be configured to detect muscle contraction, such as by monitoring electromyogram signals. Alternatively, the sensor 1031 could be an electrical, mechanical, chemical, or optical sensor.

The modulated carrier signal is demodulated by the uplink demodulator 1006 on the electrostatic shield 1002, and the uplink demodulator 1006 outputs the uplink data signal at the uplink data output 1007.

During downlink periods, the downlink modulator 1008 receives a downlink data signal at the downlink data input 1010 and load modulates the carrier signal with the downlink data by coupling the load modulation resistor 1009 to the output of the rectifier 1005 which is connected across the gap of the electrostatic shield 1002. The modulated carrier signal is demodulated by the downlink demodulator 1025 on the target device coil 1021, and the downlink demodulator outputs the downlink data signal at the downlink data output 1026.

The power transmitting device 1000 includes a system controller 1011, and the target device 1020 includes a system controller 1030. System controller 1011 may be configured to control downlink modulator 1008 and uplink demodulator 1006. System controller 1030 may be configured to control uplink modulator 1027 and downlink demodulator 2015. During periods when uplink communication is to be performed, system controller 1011 could control uplink demodulator 1006 to be active and downlink modulator 1008 to be inactive, and system controller 1030 could control uplink modulator 1027 to be active and downlink demodulator 1025 to be inactive. If multiple target devices 1020 are in use, system controller 1030 could control uplink modulator 1027 to be active during its designated transmission window. During periods when downlink communication is to be performed, system controller 1011 could control downlink modulator 1008 to be active and uplink demodulator 1006 to be inactive, and system controller 1030 could control downlink demodulator 1025 to be active and uplink modulator 1027 to be inactive.

Figure 11:
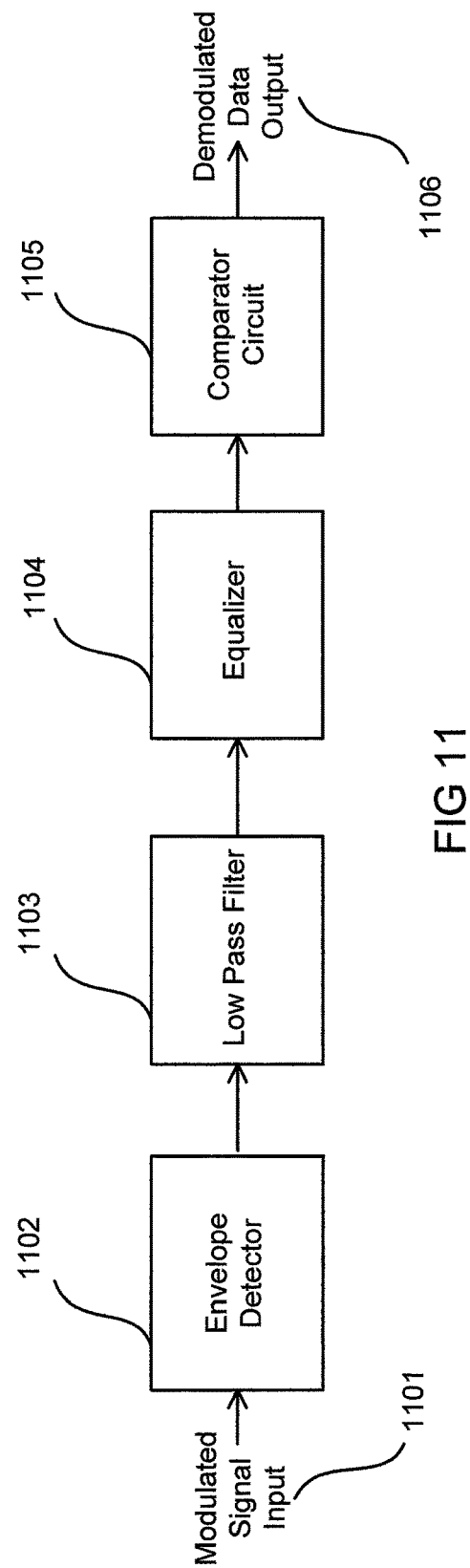
FIG. 11 is a diagram of an exemplary embodiment of a demodulator.

FIG. 11 is a diagram of an exemplary demodulator for use with the exemplary wireless power transfer and communication systems discussed above. The demodulator takes a modulated signal at its input 1101. The modulated signal is applied to an envelope detector 1102, preferably with a full wave rectifier. The envelope signal is then passed through a low pass filter 1103. The output of the low pass filter 1103 is coupled to an equalizer 1104. In some applications, it may be desirable to use a high Q coil as the primary coil, for example to reduce power consumption. This high Q coil may introduce intersymbol interference in signals modulated onto a carrier on the coil. The equalizer 1104 is configured to remove this interference. The output of the equalizer 1104 is coupled to a comparator circuit 1105. The comparator circuit 1105 may be a zero cross detector or a data slicer. The comparator circuit outputs the demodulated data signal to the demodulator output 1106.

FIG. 12 is a flow chart depicting an exemplary embodiment of a method of communicating between two coils according to the invention. In block 1201, a carrier signal is generated on the primary coil. This could be done by applying an AC drive signal from a signal driver circuit to the primary coil. The drive signal would generate a carrier signal on the primary coil which would be dependent on the characteristics of and load upon the primary coil and any coils inductively coupled to the primary coil, and which would be present on any coils inductively coupled to the primary coil.

In block 1202, data is received at a signal processor coupled to a target coil. The target coil is inductively coupled to the primary coil.

In block 1203, the data received in block 1202 is modulated onto the carrier signal. As discussed above, the carrier signal generated on the primary coil is a function of the characteristics of and load upon coils inductively coupled to the primary coil, such as this target coil. Accordingly, the signal processor coupled to the target coil can modulate the carrier signal by changing the load presented by the target coil.

In block 1204, the carrier signal is demodulated at a signal processor coupled to an electrostatic shield guarding the primary coil. The electrostatic shield is inductively coupled to the primary coil. As discussed above, the carrier signal generated on the primary coil, now modulated with the data received in block 1202, would be present on the electrostatic shield, allowing the signal processor coupled to the electrostatic shield to demodulate the carrier signal.

In block 1205, the data recovered in block 1204 is output from the signal processor that demodulated it on the electrostatic shield.

FIG. 13 is a flow chart depicting an exemplary embodiment of a method of communicating between two coils according to the invention. In block 1301, a carrier signal is generated on the primary coil. This could be done by applying an AC drive signal from a signal driver circuit to the primary coil. The drive signal would generate a carrier signal on the primary coil which would be dependent on the characteristics of and load upon the primary coil and any coils inductively coupled to the primary coil, and which would be present on any coils inductively coupled to the primary coil.

In block 1302, data is received at a signal processor coupled to an electrostatic shield guarding the primary coil. The electrostatic shield is inductively coupled to the primary coil.

In block 1303, the data received in block 1302 is modulated onto the carrier signal. As discussed above, the carrier signal generated on the primary coil is a function of the characteristics of and load upon coils inductively coupled to the primary coil, such as this electrostatic shield. Accordingly, the signal processor coupled to the electrostatic shield can modulate the carrier signal by changing the load presented by the electrostatic shield.

In block 1304, the carrier signal is demodulated at a signal processor coupled to a target device coil. The target device coil is inductively coupled to the primary coil. As discussed above, the carrier signal generated on the primary coil, now modulated with the data received in block 1302, would be present on the target coil, allowing the signal processor coupled to the target coil to demodulate the carrier signal.

In block 1305, the data recovered in block 1304 is output from the signal processor that demodulated it on the target coil.

FIG. 14 is a flow chart depicting an exemplary embodiment of a method of communicating between two coils according to the invention. In block 1401, a carrier signal is generated on the primary coil. This can be done by applying an AC drive signal from a signal driver circuit to the primary coil. The drive signal would generate a carrier signal on the primary coil which would be dependent on the characteristics of and load upon the primary coil and any coils inductively coupled to the primary coil, and which would be present on any coils inductively coupled to the primary coil.

In block 1402, data is received at a signal processor coupled to an electrostatic shield guarding a target coil. The electrostatic shield is inductively coupled to the target coil, and both the target coil and the electrostatic shield are inductively coupled to the primary coil.

In block 1403, the data received in block 1402 is modulated onto the carrier signal. As discussed above, the carrier signal generated on the primary coil is a function of the characteristics of and load upon coils inductively coupled to the primary coil, such as this electrostatic shield. Accordingly, the signal processor coupled to the electrostatic shield can modulate the carrier signal by changing the load presented by the electrostatic shield.

In block 1404, the carrier signal is demodulated at a signal processor coupled to the primary coil. The carrier signal is now modulated with the data received in block 1402, allowing the signal processor coupled to the primary coil to demodulate the carrier signal.

In block 1405, the data recovered in block 1404 is output from the signal processor coupled to the primary coil.

FIG. 15 is a flow chart depicting an exemplary embodiment of a method of communicating between two coils according to the invention. In block 1501, a carrier signal is generated on the primary coil. This can be done by applying an AC drive signal from a signal driver circuit to the primary coil. The drive signal would generate a carrier signal on the primary coil which would be dependent on the characteristics of and load upon the primary coil and any coils inductively coupled to the primary coil, and which would be present on any coils inductively coupled to the primary coil.

In block 1502, data is received at a signal processor coupled to the primary coil.

In block 1503, the data delivered in block 1502 is modulated onto the carrier signal.

In block 1504, the carrier signal is demodulated at a signal processor coupled to an electrostatic shield guarding the target device coil. The electrostatic shield is inductively coupled to the target device coil, and both target coil and the electrostatic shield are inductively coupled to the primary coil. As discussed above, the carrier signal generated on the primary coil, now modulated with the data received in block 1502, would be present on the electrostatic shield, allowing the signal processor coupled to the electrostatic shield to demodulate the carrier signal.

In block 1505, the data recovered in block 1504 is output from the signal processor coupled to the electrostatic shield.

Various uses for embodiments of wireless power transfer and communication systems according to the invention are contemplated, including interacting transcutaneously with implanted medical devices as discussed above; charging and communicating with consumer electronic devices such as smart phones, laptops, and tablets; and charging and communicating with electric vehicles, including during operation of the vehicles.

I claim:

1. A wireless power transfer and communication system comprising:
 a first coil;
 an electrostatic shield for the first coil, the electrostatic shield having a gap extending the axial length of the electrostatic shield, wherein the electrostatic shield is inductively coupled to the first coil;
 a first signal processor coupled across the gap of the electrostatic shield;
 a second coil, the second coil being inductively coupled to the first coil;
 a second signal processor coupled to the second coil; and
 a coil driver coupled to the first coil and configured to generate a carrier signal on the first coil.

2. The system of claim 1 wherein the first signal processor and the second signal processor communicate through modulation of the carrier signal.

3. The system of claim 1 wherein the first signal processor comprises a modulator configured to modulate data onto the carrier signal and the second signal processor comprises a demodulator configured to demodulate the carrier signal and output the data.

4. The system of claim 1 wherein the second signal processor comprises a modulator configured to modulate data onto the carrier signal and the first signal processor comprises a demodulator configured to demodulate the carrier signal and output the data.

5. The system of claim 1 wherein the electrostatic shield is inductively coupled to the first coil as a single turn secondary winding.

6. The system of claim 1 wherein the gap prevents the electrostatic shield from acting as a shorted turn.

7. The system of claim 1 wherein the electrostatic shield is adjacent to the outer surface of the first coil, surrounds the first coil circumferentially, and is open on both ends.

8. The system of claim 1 wherein the electrostatic shield is adjacent to the inner surface of the first coil, extends around the inner surface of the first coil circumferentially, and is open on both ends.

9. The system of claim 1 wherein the electrostatic shield has an outer portion and an inner portion, the outer portion is adjacent to the outer surface of the first coil and surrounds the first coil circumferentially, the inner portion is adjacent to the inner surface of the first coil and extends around the inner surface of the first coil circumferentially, and both the outer portion and the inner portion are open on both ends.

10. The system of claim 9 wherein the gap extends the axial length of both the outer portion and the inner portion of the electrostatic shield.

11. The apparatus of claim 1 wherein:
the electrostatic shield has a cylindrical or truncated conical structure that is open on both ends and which is coaxial with the first coil; and
the gap extends from one open end of the electrostatic shield to the other.

12. The system of claim 1 wherein a center tap of the electrostatic shield is connected to ground.

13. The system of claim 1 wherein the first coil and the electrostatic shield are configured to fit over a limb of a patient.

14. The system of claim 13 wherein the limb is a residual portion of an amputated limb.

15. The system of claim 13 wherein the electrostatic shield is positioned to reduce parasitic variations introduced on the first coil by the limb.

16. The system of claim 13 further comprising:
an implantable biological sensor providing sensor data to the second signal processor, wherein the second signal processor is configured to modulate the carrier signal with the sensor data, and the first signal processor demodulates the carrier signal and outputs received sensor data.

17. The system of claim 16 further comprising:
a prosthetic device with a prosthetic controller, wherein the prosthetic controller is coupled to the first signal processor and receives the received sensor data and generates control signals to actuate the prosthetic device.

18. A method of communicating between a first coil and a second coil, the first coil having an electrostatic shield, the first coil being inductively coupled with the electrostatic shield, the first coil being inductively coupled with the second coil, comprising:
generating a carrier signal on the first coil;
receiving an input data signal;
modulating the carrier signal with the data from the input data signal on the second coil;
demodulating the carrier signal on the electrostatic shield; and
outputting an output data signal comprising the data demodulated from the carrier signal.

19. The method of claim 18 wherein modulating the carrier signal on the second coil is changing the impedance presented to the first coil by the second coil.

20. The method of claim 18 wherein the input data signal is sensor data received from a biological sensor.

21. The method of claim 18 further comprising:
actuating a prosthetic device based on the output data signal.

22. A method of communicating between a first coil and a second coil, the first coil having an electrostatic shield, the first coil being inductively coupled with the electrostatic shield, the first coil being inductively coupled with the second coil, comprising:
generating a carrier signal on the first coil;
receiving an input data signal;
modulating the carrier signal with the data from the input data signal on the electrostatic shield;
demodulating the carrier signal on the second coil; and
outputting an output data signal comprising the data demodulated from the carrier signal.

23. The method of claim 22 wherein modulating the carrier signal on the electrostatic shield is changing the impedance presented to the first coil by the electrostatic shield.

24. A wireless power transfer and communication apparatus comprising:
a first coil;
a coil driver circuit, the coil driver circuit being coupled to the first coil and configured to generate a carrier signal on the first coil;
an electrostatic shield for the first coil, the electrostatic shield having a gap extending the axial length of the electrostatic shield, wherein the electrostatic shield is inductively coupled to the first coil; and
a demodulator connected across the gap of the electrostatic shield, wherein the demodulator demodulates the carrier signal.

25. The apparatus of claim 24 wherein the first coil inductively couples to a second coil, and wherein the carrier signal is modulated by changing the impedance of the second coil.

26. The apparatus of claim 24 further comprising:
an implantable biological sensor providing sensor data to a modulator, wherein the modulator is coupled to a second coil, the second coil being inductively coupled to the first coil, and wherein the modulator is configured to modulate the carrier signal with the sensor data.

27. The apparatus of claim 24 further comprising:
a prosthetic device with a prosthetic controller, wherein the prosthetic controller is coupled to the demodulator and generates control signals to actuate the prosthetic device based on the demodulated carrier signal.

28. The apparatus of claim 24 wherein the electrostatic shield is inductively coupled to the first coil as a single turn secondary coil.

29. The apparatus of claim 24 wherein the gap prevents the electrostatic shield from acting as a shorted turn.

30. The apparatus of claim 24 wherein:
the electrostatic shield has a cylindrical or truncated conical structure that is open on both ends and which is coaxial with the first coil; and
wherein the gap extends from one open end of the electrostatic shield to the other.

31. The apparatus of claim 24 wherein the electrostatic shield is adjacent to the outer surface of the first coil, surrounds the first coil circumferentially and is open on both ends.

32. The apparatus of claim 31 wherein the gap extends from one open end of the electrostatic shield to the other.

33. The apparatus of claim 24 wherein the electrostatic shield is adjacent to the inner surface of the first coil, extends around the inner surface of the first coil circumferentially, and is open on both ends.

34. The apparatus of claim 33 wherein the gap extends from one open end of the electrostatic shield to the other.

35. The apparatus of claim 24 wherein a center tap of the electrostatic shield is connected to ground.

36. The apparatus of claim 24 wherein the first coil and the electrostatic shield are configured to fit over a limb of a patient.

37. The apparatus of claim 36 wherein the limb is a residual portion of an amputated limb.

38. A wireless power transfer and communication apparatus comprising:
- a first coil;
- a coil driver circuit, the coil driver circuit being coupled to the first coil and configured to generate a carrier signal on the first coil;
- an electrostatic shield for the first coil, the electrostatic shield having a gap extending the axial length of the electrostatic shield, wherein the electrostatic shield is inductively coupled to the first coil; and
- a modulator connected across the gap of the electrostatic shield, wherein the modulator modulates the carrier signal.

39. The apparatus of claim 38 wherein the electrostatic shield is inductively coupled to the first coil as a single turn secondary coil.

40. The apparatus of claim 38 wherein the gap prevents the electrostatic shield from acting as a shorted turn.

41. The apparatus of claim 38 wherein:
- the electrostatic shield has a cylindrical or truncated conical structure that is open on both ends and which is coaxial with the first coil; and
- wherein the gap extends from one open end of the electrostatic shield to the other.

42. The apparatus of claim 38 wherein the electrostatic shield is adjacent to the outer surface of the first coil, surrounds the first coil circumferentially and is open on both ends.

43. The apparatus of claim 42 wherein the gap extends from one open end of the electrostatic shield to the other.

44. The apparatus of claim 38 wherein the electrostatic shield is adjacent to the inner surface of the first coil, extends around the inner surface of the first coil circumferentially, and is open on both ends.

45. The apparatus of claim 44 wherein the gap extends from one open end of the electrostatic shield to the other.

46. The apparatus of claim 38 wherein a center tap of the electrostatic shield is connected to ground.

47. The apparatus of claim 38 wherein the first coil and the electrostatic shield are configured to fit over a limb of a patient.

48. The apparatus of claim 47 wherein the limb is a residual portion of an amputated limb.

* * * * *